US009845357B2

(12) United States Patent
Nishimura et al.

(10) Patent No.: US 9,845,357 B2
(45) Date of Patent: *Dec. 19, 2017

(54) INTEGRIN αVβ8 NEUTRALIZING ANTIBODY

(71) Applicant: The Regents of the University of California, Oakland, CA (US)

(72) Inventors: Stephen Nishimura, Mill Valley, CA (US); Jianlong Lou, San Bruno, CA (US); Jody Lynn Baron, Mill Valley, CA (US); James D. Marks, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/003,642

(22) Filed: Jan. 21, 2016

(65) Prior Publication Data

US 2016/0137737 A1 May 19, 2016

Related U.S. Application Data

(62) Division of application No. 13/580,105, filed as application No. PCT/US2011/025514 on Feb. 8, 2011, now Pat. No. 9,290,572.

(60) Provisional application No. 61/305,749, filed on Feb. 18, 2010, provisional application No. 61/428,814, filed on Dec. 30, 2010.

(51) Int. Cl.
*C07K 16/28* (2006.01)
*G01N 33/68* (2006.01)
*A61K 39/00* (2006.01)

(52) U.S. Cl.
CPC ..... *C07K 16/2839* (2013.01); *G01N 33/6854* (2013.01); *A61K 2039/505* (2013.01); *C07K 2317/34* (2013.01); *C07K 2317/76* (2013.01); *G01N 2333/70546* (2013.01)

(58) Field of Classification Search
None
See application file for complete search history.

(56) References Cited

U.S. PATENT DOCUMENTS

| | | | | |
|---|---|---|---|---|
| 4,816,567 | A | 3/1989 | Cabilly et al. | |
| 5,530,101 | A | 6/1996 | Queen et al. | |
| 7,087,405 | B2 | 8/2006 | Johanson et al. | |
| 7,354,584 | B2 | 4/2008 | Reed | |
| 8,198,412 | B2 | 6/2012 | Kojima et al. | |
| 9,290,572 | B2 * | 3/2016 | Nishimura | C07K 16/2839 |
| 9,492,569 | B2 * | 11/2016 | Nishimura | C07K 14/70546 |
| 2004/0170630 | A1 | 9/2004 | Huang et al. | |
| 2009/0324604 | A1 | 12/2009 | Liu et al. | |

FOREIGN PATENT DOCUMENTS

WO 2010/022737 A1 3/2010

OTHER PUBLICATIONS

Tsui et al. The TGF-b inhibitory activity of antibody 37E1B5 depends on its H-CDR2 glycan. MABS, 2017, vol. 9, No. 1, 104-113 (Year: 2017).*
Mu et al. The integrin αvβ8 mediates epithelial homeostasis through MT1-MMP-dependent activation of TGF-β1. The Journal of Cell Biology, vol. 157, No. 3, Apr. 29, 2002 493-507. (Year: 2002).*
Araya et al.; "Intergrin-Mediated Transforming Growth Factor-β Activation Regulates Homeostasis of the Pulmonary Epithelial-Mesenchymal Trophic Unit"; *Am. J. Pathol.*; 169:405-415 (2008).
Cambier et al.; "A role for the integrin alphavbeta8 in the negative regulation of epithelial cell growth"; *Cancer Res.*; 60(24):7084-7093 (2000).
Cambier et al.; "Integrin alpha(v)beta8-mediated activation of transforming growth factor-beta by perivascular astrocytes: an angiogenic control switch" *Am. J. Pathol.*; 166(6):1883-1894 (2005).
Fjellbirkeland et al.; "Integrin alphavbeta8-mediated activation of transforming growth factor-beta inhibits human airway epithelial proliferation in intact bronchial tissue"; *Am. J. Pathol.*; 163(2):533-542 (2003).
Office Action from CN 201180018213.9, dated Dec. 25, 2013 (English translation only).
Supplementary European Search Report from EP 11745373 dated Nov. 28, 2013.
International Search Report and Written Opinion from PCT/US2012/051373, dated Feb. 4, 2013.
International Search Report from PCT/US2011/025514, dated Aug. 31, 2011.

Mu et al.; "The integrin αvβ8 mediates epithelial homeostasis through MT1-MMP-dependent activation of TGF-β1"; J. Cell. Biol.; 157(3):493-507 (2002).

Neurohr et al.; "Activation of transforming growth factor-beta by the integrin alphavbeta8 delays epithelial wound closure"; *Am. J. Respir. Cell Mol. Biol.*; 35(2):252-9 (2006). Epub Mar. 30, 2006.
Nishimura, SL; "Integrin-mediated transforming growth factor-beta activation, a potential therapeutic target in fibrogenic disorders"; *Am J Pathol.*; 175(4):1362-1370 (2009). Epub Sep. 3, 2009.
Razai et al. Molecular evolution of antibody affinity for sensitive detection of botulinum neurotoxin type A. J Mol Bioi 351 :158-169, 2005.

(Continued)

*Primary Examiner* — Maher M Haddad

(74) *Attorney, Agent, or Firm* — Kilpatrick Townsend & Stockton LLP

(57) ABSTRACT

The present invention relates to αvβ8 antagonists, anti-αvβ8 antibodies or immunoconjugates for reducing TGFβ activation in an individual. Further provided are compositions comprising one of the αvβ8 antagonists, anti-αvβ8 antibodies or immunoconjugates, methods for using the compositions, and related subject matter.

11 Claims, No Drawings

(56) References Cited

OTHER PUBLICATIONS

UniProt Accession No. P26012, "ITB8_HUMAN"; Feb. 9, 2012 (4 pages).
US Biological Technical Data Sheet, No. I7661-37E1; "Integrin alphaV, beta 3 (PE)"; No date (1 page) Retrieved from the internet at usbio.net/technicalsheet.php?item=I7661-37E1 (Aug. 9, 2011).
Wu et al. Stepwise in vitro affinity maturation of Vitaxin, an αvβ3-specific humanized mAb. Proc. Natl. Acad. Sci. USA vol. 95, pp. 6037-6042, May 1998.

\* cited by examiner

SEQUENCE LISTING

<160> NUMBER OF SEQ ID NOS: 12

<210> SEQ ID NO 1
<211> LENGTH: 116
<212> TYPE: PRT
<213> ORGANISM: Artificial
<220> FEATURE:
<223> OTHER INFORMATION: Synthetic peptide of engineered variable heavy
      region of clone 37E1 from Mus musculus

<400> SEQUENCE: 1

Glu Val Gln Leu Val Glu Ser Gly Gly Gly Leu Val Gln Pro Gly Gly
1               5                   10                  15

Ser Leu Asn Leu Ser Cys Ala Ala Ser Gly Phe Val Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Ser Ser Leu
    50                  55                  60

Lys Asp Lys Phe Ile Ile Ser Arg Asp Asn Ala Lys Asn Thr Leu Tyr
65                  70                  75                  80

Leu Gln Met Asn Lys Val Arg Ser Glu Asp Thr Ala Leu Tyr Tyr Cys
                85                  90                  95

Ala Cys Leu Ile Thr Thr Glu Asp Tyr Trp Gly Gln Gly Thr Ser Val
            100                 105                 110

Thr Val Ser Ser
        115

<210> SEQ ID NO 2
<211> LENGTH: 116
<212> TYPE: PRT
<213> ORGANISM: Artificial
<220> FEATURE:
<223> OTHER INFORMATION: Synthetic peptide of engineered variable heavy
      region of clone 37E1b5 from Mus musculus

<400> SEQUENCE: 2

Glu Val Gln Leu Val Glu Ser Gly Gly Gly Leu Val Gln Pro Gly Gly
1               5                   10                  15

Ser Leu Asn Leu Ser Cys Ala Val Ser Gly Phe Val Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Ser Ser Leu
    50                  55                  60

Lys Asp Lys Phe Ile Ile Ser Arg Asp Asn Ala Lys Asn Thr Leu Tyr
65                  70                  75                  80

Leu Gln Met Asn Lys Val Arg Ser Glu Asp Thr Ala Leu Tyr Tyr Cys
                85                  90                  95

Ala Cys Leu Ile Thr Thr Glu Asp Tyr Trp Gly Gln Gly Thr Ser Val
            100                 105                 110

Thr Val Ser Ser
        115

<210> SEQ ID NO 3
<211> LENGTH: 108
<212> TYPE: PRT
<213> ORGANISM: Artificial
<220> FEATURE:
<223> OTHER INFORMATION: Synthetic peptide of engineered variable light -continued region of clone 37E1 from Mus musculus

<400> SEQUENCE: 3

Gln Ile Val Leu Thr Gln Ser Pro Ser Ser Met Tyr Ala Ser Leu Gly
1               5                   10                  15
Glu Arg Val Thr Ile Pro Cys Lys Ala Ser Gln Asp Ile Asn Ser Tyr
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Tyr
                85                  90                  95
Thr Phe Gly Gly Gly Thr Lys Leu Glu Ile Lys Ala
            100                 105

<210> SEQ ID NO 4
<211> LENGTH: 108
<212> TYPE: PRT
<213> ORGANISM: Artificial
<220> FEATURE:
<223> OTHER INFORMATION: Synthetic peptide of engineered variable light
      region of clone 37E1B5 from Mus musculus

<400> SEQUENCE: 4

Gln Ile Val Leu Thr Gln Ser Pro Ser Ser Met Tyr Ala Ser Leu Gly
1               5                   10                  15
Glu Arg Val Thr Ile Pro Cys Lys Ala Ser Gln Asp Ile Asn Ser Tyr
            20                  25                  30
Leu Ser Trp Phe Gln Gln Lys Pro Gly Lys Ser Pro Lys Thr Leu Ile
        35                  40                  45
Tyr Tyr Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Tyr
                85                  90                  95
Thr Phe Gly Gly Gly Thr Lys Leu Glu Ile Lys Ala
            100                 105

<210> SEQ ID NO 5
<211> LENGTH: 5
<212> TYPE: PRT
<213> ORGANISM: Artificial
<220> FEATURE:
<223> OTHER INFORMATION: Synthetic peptide of CDR1 of engineered
      variable heavy region of Mus musculus clone 37E1 or 37E1b5

<400> SEQUENCE: 5

Arg Tyr Trp Met Ser
1               5

<210> SEQ ID NO 6
<211> LENGTH: 17
<212> TYPE: PRT
<213> ORGANISM: Artificial
<220> FEATURE:
<223> OTHER INFORMATION: Synthetic peptide of CDR2 of engineered
      variable heavy region of Mus musculus clone 37E1 or 37E1b5

```
<400> SEQUENCE: 6

Glu Ile Asn Pro Asp Ser Ser Thr Ile Asn Tyr Thr Ser Ser Leu Lys
1               5                   10                  15

Asp

<210> SEQ ID NO 7
<211> LENGTH: 7
<212> TYPE: PRT
<213> ORGANISM: Artificial
<220> FEATURE:
<223> OTHER INFORMATION: Synthetic peptide of CDR3 of engineered
      variable heavy region of Mus musculus clone 37E1 or 37E1b5

<400> SEQUENCE: 7

Leu Ile Thr Thr Glu Asp Tyr
1               5

<210> SEQ ID NO 8
<211> LENGTH: 11
<212> TYPE: PRT
<213> ORGANISM: Artificial
<220> FEATURE:
<223> OTHER INFORMATION: Synthetic peptide of CDR1 of engineered
      variable light region of Mus musculus clone 37E1 or 37E1b5

<400> SEQUENCE: 8

Lys Ala Ser Gln Asp Ile Asn Ser Tyr Leu Ser
1               5                   10

<210> SEQ ID NO 9
<211> LENGTH: 7
<212> TYPE: PRT
<213> ORGANISM: Artificial
<220> FEATURE:
<223> OTHER INFORMATION: Synthetic peptide of CDR2 of engineered
      variable light region of Mus musculus clone 37E1 or 37E1b5
<220> FEATURE:
<221> NAME/KEY: MISC_FEATURE
<222> LOCATION: (1)..(1)
<223> OTHER INFORMATION: Xaa can be Arg or Tyr

<400> SEQUENCE: 9

Xaa Ala Asn Arg Leu Val Asp
1               5

<210> SEQ ID NO 10
<211> LENGTH: 9
<212> TYPE: PRT
<213> ORGANISM: Artificial
<220> FEATURE:
<223> OTHER INFORMATION: Synthetic peptide of CDR3 of engineered
      variable light region of Mus musculus clone 37E1 or 37E1b5

<400> SEQUENCE: 10

Leu Gln Tyr Asp Glu Phe Pro Tyr Thr
1               5

<210> SEQ ID NO 11
<211> LENGTH: 107
<212> TYPE: PRT
<213> ORGANISM: Homo sapiens

<400> SEQUENCE: 11

Ile Ser Gly Gly Ser Arg Ser Glu Arg Cys Asp Ile Val Ser Asn Leu
1               5                   10                  15
```

```
Ile Ser Lys Gly Cys Ser Val Asp Ser Ile Glu Tyr Pro Ser Val His
            20                  25                  30

Val Ile Ile Pro Thr Glu Asn Glu Ile Asn Thr Gln Val Thr Pro Gly
        35                  40                  45

Glu Val Ser Ile Gln Leu Arg Pro Gly Ala Glu Ala Asn Phe Met Leu
    50                  55                  60

Lys Val His Pro Leu Lys Lys Tyr Pro Val Asp Leu Tyr Tyr Leu Val
65                  70                  75                  80

Asp Val Ser Ala Ser Met His Asn Asn Ile Glu Lys Leu Asn Ser Val
                85                  90                  95

Gly Asn Asp Leu Ser Arg Lys Met Ala Phe Phe
                100                 105

<210> SEQ ID NO 12
<211> LENGTH: 107
<212> TYPE: PRT
<213> ORGANISM: Mus musculus

<400> SEQUENCE: 12

Val Ser Gly Gly Ser Gly Ser Glu Arg Cys Asp Thr Val Ser Ser Leu
1               5                   10                  15

Ile Ser Lys Gly Cys Pro Val Asp Ser Ile Glu Tyr Leu Ser Val His
            20                  25                  30

Val Val Thr Ser Ser Glu Asn Glu Ile Asn Thr Gln Val Thr Pro Gly
        35                  40                  45

Glu Val Ser Val Gln Leu His Pro Gly Ala Glu Ala Asn Phe Met Leu
    50                  55                  60

Lys Val Arg Pro Leu Lys Lys Tyr Pro Val Asp Leu Tyr Tyr Leu Val
65                  70                  75                  80

Asp Val Ser Ala Ser Met His Asn Asn Ile Glu Lys Leu Asn Ser Val
                85                  90                  95

Gly Asn Asp Leu Ser Lys Lys Met Ala Leu Tyr
                100                 105
```

INTEGRIN αVβ8 NEUTRALIZING ANTIBODY

CROSS-REFERENCES TO RELATED APPLICATIONS

The present application is a divisional application of U.S. application Ser. No. 13/580,105, filed Nov. 19, 2012, now U.S. Pat. No. 9,290,572, issued on Mar. 22, 2016 which is a §371 of PCT/US2011/025514, filed Feb. 8, 2011 and claims priority to U.S. Provisional Application No. 61/305,749, filed Feb. 18, 2010, and U.S. Provisional Application No. 61/428,814, filed Dec. 30, 2010, all the disclosures of which are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Grant No. HL63993 and NS044155 awarded by the National Institutes of Health. The Government has certain rights in this invention.

BACKGROUND OF THE INVENTION

The multifunctional cytokine transforming growth factor-β (TGF-β) plays major roles in the biology of immune, endothelial, epithelial, and mesenchymal cells during development and adult life in invertebrate and vertebrate species. In mammals, these functions are mediated by three isoforms, TGF-β1, 2, and 3, which are each widely expressed. All three isoforms interact with the same cell surface receptors (TGFBR2 and ALK5) and signal through the same intracellular signaling pathways, which involve either canonical (i.e., SMADs) or noncanonical (i.e., MAPK, JUN, PI3K, PP2A, Rho, PAR6) signaling effectors. The canonical TGF-β signaling pathway, whereby TGF-β signaling is propagated from the TGF-β receptor apparatus through phosphorylation of cytoplasmic SMAD-2/3, complex formation with SMAD-4, nuclear translocation of the SMAD-2/3/4 complex, and binding to SMAD response elements located in the promoter regions of many genes involved in the fibrogenic response, has been the most intensively studied. However, despite having similar signaling partners, each isoform serves individual biological functions, perhaps due to differences in binding affinity to TGF-β receptors, activation mechanism, signaling intensity or duration, or spatial and/or temporal distribution.

Knockout and conditional deletion models of TGF-β isoforms, receptors, and signaling mediators, as well as function-blocking reagents targeting all TGF-β isoforms, have revealed essential roles for TGF-β in T-cell, cardiac, lung, vascular, and palate development. For instance, mice deficient in TGF-β1 either die in utero owing to defects in yolk sac vasculogenesis or are born and survive into adult life but develop severe multiorgan autoimmunity. Genetic deletion of TGF-β signaling mediators has shown an essential role for Smad2 in early patterning and mesodermal formation, and mice lacking Smad3 are viable and fertile, but exhibit limb malformations, immune dysregulation, colitis, colon carcinomas, and alveolar enlargement. In adult tissues, the TGF-β pathway is thought to regulate the dynamic interactions among immune, mesenchymal, and epithelial cells to maintain homeostasis in response to environmental stress.

The normal homeostatic pathways mediated by TGF-β are perturbed in response to chronic repetitive injury. In cases of injury, TGF-β becomes a major profibrogenic cytokine, delaying epithelial wound healing by inhibiting epithelial proliferation and migration and promoting apoptosis and expanding the mesenchymal compartment by inducing fibroblast recruitment, fibroblast contractility, and extracellular matrix deposition. Indeed, intratracheal transfer of adenoviral recombinant TGF-β1 to the rodent lung dramatically increases fibroblast accumulation and expression of type I and type III collagen around airways and in the pulmonary interstitium, and neutralizing anti-TGF-β antibodies can block experimental bleomycin or radiation-induced pulmonary fibrosis.

Increased activity of the TGF-β pathway has also been implicated in fibrotic lung disease, glomerulosclerosis, and restenosis of cardiac vessels. Most TGF-β-mediated pathological changes appear to be attributed to the TGF-β1 isoform. The complexity of TGF-β1 function in humans is illuminated by hereditary disorders with generalized or cell-type specific enhancement or deficiency in either TGF-β1 itself or its signaling effectors. Mutations that increase the activity of the TGF-β pathway lead to defects in bone metabolism (i.e., Camurati-Engelmann disease) and in connective tissue (i.e., Marfan syndrome), and in aortic aneurysms (i.e., Loeys-Dietz syndrome), whereas mutations that lead to decreased activity of the TGF-β pathway correlate with cancer occurrence and prognosis. The role of TGF-β as a tumor suppressor in cancer is not straightforward, however, because TGF-β can also enhance tumor growth and metastasis, perhaps through its roles in immune suppression, cell invasion, epithelial-mesenchymal transition, or angiogenesis.

Despite the multiple essential functions of TGF-β, a single dose or short-term administration of a pan-TGF-β neutralizing antibody is reportedly well tolerated at doses that inhibit organ fibrosis or experimental carcinoma cell growth and metastasis, with no reported side effects in adult mice and rats. This treatment has shown therapeutic efficacy in inhibiting experimental fibrosis. Because of these promising results, single-dose phase I/II clinical trials using neutralizing pan-TGF-β antibodies have been performed or are ongoing for metastatic renal cell carcinoma, melanoma, focal segmental glomerulosclerosis, and idiopathic pulmonary fibrosis (Genzyme Corporation, genzymeclinicalresearch.com, last accessed Aug. 27, 2009). Careful targeting of the TGF-β pathway to minimize systemic effects is a highly desirable goal.

BRIEF SUMMARY OF THE INVENTION

The present invention is directed to a method of reducing TGFβ activation in an individual, e.g., a human or a non-human, by administering an antagonist of integrin αvβ8 to an individual in need thereof, thereby reducing TGFβ activation in the individual. In some embodiments, the antagonist reduces TGFβ activation (e.g., recruitment of a protease that cleaves latent TGFβ thereby releasing the mature, active TGFβ peptide) but does not significantly inhibit αvβ8 adhesion to TGFβ (e.g., adhesion of αvβ8 expressed on a cell surface to latent TGFβ associated with the cell matrix).

In some embodiments, the antagonist is an antibody. Thus, the invention provides for isolated antibodies that inhibit release of active, mature TGFβ peptide (TGFβ activation), but do not significantly inhibit adhesion of TGFβ to αvβ8 on a αvβ8-expressing cell. In some embodiments, the antibody specifically binds to αvβ8, e.g., specifically to β8.

In some embodiments, the antibody binds to an epitope on β8 that is within SEQ ID NO: 11. In some embodiments, the epitope includes at least one amino acid selected from amino acids I125, R128, R175, F179, and F180 of human 38. In some embodiments, the antibody binds at least one amino acid selected from amino acids R79, I85, S95, P100, I108, P109, R128, H140, and F179 of human J38. In some embodiments, the antibody binds at least one amino acid selected from amino acids 174, N88, I107, T110, I125, R175, and F180 of human J38. In some embodiments, the antibody binds human, but not mouse β8. In some embodiments, the antibody reduces TGFβ activation but does not significantly inhibit αvβ8-mediated cell adhesion to TGFβ.

In some embodiments, the antibody competes for binding to αvβ8 with an antibody having a light chain variable region comprising three light chain CDRs of SEQ ID NO: 5, SEQ ID NO: 6, and SEQ ID NO: 7, and a heavy chain variable region comprising three heavy chain CDRs of SEQ ID NO: 8, SEQ ID NO: 9, SEQ ID NO: 10. In some embodiments, the antibody has a light chain variable region comprising three light chain CDRs of SEQ ID NO: 5, SEQ ID NO: 6, and SEQ ID NO: 7, and a heavy chain variable region comprising three heavy chain CDRs of SEQ ID NO: 8, SEQ ID NO: 9, SEQ ID NO: 10. For example, in some embodiments, the antibody has a light chain variable region of SEQ ID NO:3 or 4 and a heavy chain variable region of SEQ ID NO: 1 or 2. Specific examples of the antibody of the invention include an antibody having a light chain variable region of SEQ ID NO:3 and a heavy chain variable region of SEQ ID NO: 1, and an antibody has a light chain variable region of SEQ ID NO:4 and a heavy chain variable region of SEQ ID NO:2.

The antibody can be of various isotypes, e.g., IgG1, IgG2, IgG2a, IgG3 or IgG4. A monoclonal or polyclonal antibody can be used. In some embodiments, the antibody is human, humanized or chimeric antibody.

The present invention further provides for an isolated nucleic acid, a vector or vectors, and host cells suitable for encoding the antibody of the present invention.

The present invention further relates to a pharmaceutical composition comprising the antibody of the present invention and a pharmaceutically acceptable excipient. In some embodiments, the pharmaceutical composition is a diagnostic, e.g., comprising a labeled antibody. In some embodiments, the pharmaceutical composition is therapeutic.

In some embodiments, the antibody is used for detection, e.g., to determine the presence of β8 in vivo or in vitro. In such embodiments, the antibody is labeled directly or indirectly with a detectable moiety. Thus, in some embodiments, the invention provides methods of determining the presence of integrin β8 in a biological sample (in vitro or in vivo) comprising contacting the biological sample with a labeled antibody according to the invention and detecting the presense of the labeled antibody, thereby determining the presence of integrin β8. In some embodiments, the method is used to diagnose a condition selected from the group consisting of arthritis, chronic obstructive pulmonary disease (COPD), asthma, fibrotic disorders, an inflammatory brain autoimmune disease, multiple sclerosis, a demylinating disease (e.g., transverse myelitis, Devic's disease, Guillain-Barré syndrome), neuroinflammation, kidney disease, adenocarcinoma, squamous carcinoma, glioma, breast carcinoma, and cancer growth and metastasis.

The present invention further relates to a transgenic mouse that expresses human integrin β8. In some embodiments, the transgenic mouse of the invention does not express mouse integrin β8.

The compositions and methods of the invention can be used to reduce TGFβ activation in an individual having one or more of condition selected from the group consisting of arthritis, chronic obstructive pulmonary disease (COPD), asthma, fibrotic disorders, an inflammatory brain autoimmune disease, multiple sclerosis, a demylinating disease (e.g., transverse myelitis, Devic's disease, Guillain-Barré syndrome), neuroinflammation, kidney disease, adenocarcinoma, squamous carcinoma, glioma, breast carcinoma, and cancer growth and metastasis, and wherein TGFβ reduction results in amelioration of the condition. In some embodiments, the fibrotic disorders is airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, crytogenic organizing pneumonia, chronic hypersensitivity pneumonia, drug-related lung fibrosis, renal fibrosis, or liver fibrosis.

DETAILED DESCRIPTION OF THE INVENTION

Introduction

The present invention is based, in part, on the discovery that certain anti-αvβ8 antagonists, anti-αvβ8 antibodies or immunoconjugates selectively perturbs the αvβ8-mediated activation of TGF-β, but not cell adhesion of an αvβ8-expressing cell to immobilized TGF-β. Accordingly, the present invention provides for methods of reducing TGFβ activation in an individual by administering an antagonist of αvβ8 (e.g., small molecules, anti-αvβ8 antibodies or immunoconjugates) to an individual in need thereof, thereby reducing TGFβ activation in the individual. The present invention also provides for novel antibodies having a light chain variable region comprising three light chain CDRs of SEQ ID NO: 5, SEQ ID NO: 6, and SEQ ID NO: 7, and a heavy chain variable region comprising three heavy chain CDRs of SEQ ID NO: 8, SEQ ID NO: 9, SEQ ID NO: 10.

Definitions

The term "integrin β8" is used interchangeably with itgb8, ITGB8, β8, and like terms. ITGB8 is typically used to refer to the human sequence, while itgb8 refers to the mouse sequence. The human protein sequence can be found at Uniprot accession number P26012, while the murine sequence has Uniprot accession number Q0VBD0.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention. An antagonist can neutralize activity (e.g., prevent binding and activation by a natural ligand) or actively reduce activity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." The present invention provides for, e.g., antibodies having polynucleotide or polypeptide sequences that have at least 80% identity, preferably 85%, 90%, 91%, 92%, 93, 94%, 95%, 96%, 97%, 98%, 99%, or 100% identity, to a reference sequence, e.g., SEQ ID NOs: 1-10. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The antibody binds to an epitope on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3 ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a αvβ8 positive cell, particularly cells, which express the αvβ8. Such differences can be readily apparent when viewing the bands of gels with approximately similarly loaded with test and controls samples. Examples of cytotoxic agents include, but are not limited to ricin, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the invention provides antibodies to αvβ8. Anti-αvβ8 antibodies may be used systemically to reduce TGFβ activation in an individual alone or when conjugated with a detectable label or effector moiety. Anti-αvβ8 antibodies conjugated with toxic agents, such as ricin, as well as unconjugated antibodies may be useful therapeutic agents.

Additionally, the recombinant protein of the invention comprising the antigen-binding region of any of the monoclonal antibodies of the invention can be used to detect or treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, ricin, abrin, glucocorticoid and radioisotopes.

A "label" or a "detectable moiety" is a diagnostic agent or component detectable by spectroscopic, radiological, photochemical, biochemical, immunochemical, chemical, or other physical means. Exemplary labels include radiolabels (e.g., $^{111}$In, $^{99m}$Tc, $^{131}$I, $^{67}$Ga) and other FDA-approved imaging agents. Additional labels include $^{32}$P, fluorescent dyes, electron-dense reagents, enzymes, biotin, digoxigenin, or haptens and proteins or other entities which can be made detectable, e.g., by incorporating a radiolabel into the targeting agent. Any method known in the art for conjugating a nucleic acid or nanocarrier to the label may be employed, e.g., using methods described in Hermanson, *Bioconiugate Techniques* 1996, Academic Press, Inc., San Diego.

A "labeled" or "tagged" antibody or agent is one that is bound, either covalently, through a linker or a chemical bond, or noncovalently, through ionic, van der Waals, electrostatic, or hydrogen bonds to a label such that the presence of the antibody or agent may be detected by detecting the presence of the label bound to the antibody or agent.

Techniques for conjugating detectable and therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The term "reduce," "reducing," or "reduction," when used in the context of αvβ8-mediate TGFβ activation refers to any detectable negative change or decrease in quantity of a parameter that reflects TGFβ activation, compared to a standard value obtained under the same conditions but in the absence of an agent as described herein (e.g., anti-αvβ8 antagonists, anti-αvβ8 antibodies and immunoconjugates). The level of this decrease following exposure to an agent as described herein (e.g., anti-αvβ8 antagonists, anti-αvβ8 antibodies and immunoconjugates) is, in some embodiments, at least 10% or 20%, and more preferably at least 30%, 40%, 50%, 60%, 70%, 80%, or 90%, and most preferably 100%.

The term "compete", as used herein with regard to an antibody, means that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, *Antibodies, A Laboratory Manual*, Cold Spring Harbor Press (1988)); solid phase direct label RIA using I-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

TGFβ Activation

The transforming growth factor β (TGFβ) was originally characterized as a protein (secreted from a tumor cell line) that was capable of inducing a transformed phenotype in non-neoplastic cells in culture. This effect was reversible, as demonstrated by the reversion of the cells to a normal phenotype following removal of the TGFβ. Today, TGFβ1-TGFβ5 have been identified. These proteins share similar amino acid regions.

TGFβs have proliferative effects on many mesenchymal and epithelial cell types. Under certain conditions TGFβ demonstrates anti-proliferative effects on epithelial cells, endothelial cells, macrophages, and T- and B-lymphocytes. Such effects include decreasing the secretion of immunoglobulin and suppressing hematopoiesis, myogenesis, adipogenesis, and adrenal steroidogenesis. Several members of the TGFβ family are potent inducers of mesodermal differentiation in early embryos, in particular TGF-β and activin A.

TGFβs, specifically TGFβ 1, 2, and 3, are multipotent cytokines that are important modulators of cell growth, inflammation, matrix synthesis, the immune system, angiogenesis, and apoptosis (Taipale et al.). Defects in TGFβ function are associated with a number of pathological states including immunosuppression, tumor cell growth, fibrosis, and autoimmune disease (Blobe et al.). The TGFβs are the prototypes of the TGFβ superfamily that consists of over 40 members that control key events in early development, patterning, tissue repair and wound healing. TGFβ is released as part of a latent complex in which the cytokine cannot interact with its receptor.

For TGFβ to signal, it must be released from its inactive complex by a process called TGFβ activation. The latent TGF complex includes 3 components: the active (mature) TGFβ dimmer, LAP (latency associated peptide) and LTBP (latent TGFβ binding protein). LAP is a diS bonded dimer that represents the N-terminal end of the TGFβ precursor protein. The mature TGFβ protein represent the C terminal end (about 25 kD) of the precursor. The bond between the TGFβs and LAP is proteolytically cleaved within the Golgi, but the TGF-β propeptide remains bound to TGFβ by non-covalent interactions. The complex of TGFβ and LAP is called the small latent complex (SLC). It is the association of LAP and TGFβ that confers latency. LAP-TGFβ binding is reversible and the isolated purified components can recombine to form an inactive SLC. Both the SLC and the larger complex are referred to herein as latent TGFβ, as both are inactive.

An unusual property of TGFβ is that its activity is limited by the conversion of latent TGFβ to active TGFβ (a process termed latent TGFβ activation). Tissues contain significant quantities of latent TGFβ and activation of only a small fraction of this latent TGFβ generates maximal cellular responses (Annes et al. (2003) *J. Cell Sci.* 116:217). Latency is conferred by the non-covalent interaction of the TGFβ propeptide, also called the latency associated protein (LAP). Activation occurs upon cleavage of the bond between mature TGFβ and LAP. Latent TGFβ is thus a protein precursor of the mature, active TGFβ. Once active, TGFβ binds and brings together its high affinity serine/threonine kinase type I and type II receptors and initiates a signal transduction cascade.

There is the difference between the terms "TGFβ activation" and "TGFβ processing." For the TGF-βs, the term "TGFβ processing" refers to the proteolytic cleavage of the bond between TGF-β and LAP. Without cleavage, no TGF-β activity can be detected in the precursor TGF-β dimer under any conditions. Cleavage is a prerequisite for TGFβ activity. The term "TGFβ activation" refers to the liberation of the TGF-β dimer from its interaction with LAP. Therefore, the "processed" TGF-β precursor has the potential to be activated, i.e. to release TGF-β, whereas the unprocessed TGF-β cannot be activated without initially cleaving (processing) the propeptide bond.

Several molecules have been described as latent TGFβ activators. The first cell-mediated activation process in which several cell types converted the LLC, which is produced constitutively by most cells, into active TGFβ by a protease-dependant reaction was by proteases. Latent TGFβ activation required a) the protease urokinase plasminogen activator (uPA), b) activation of uPA's substrate plasminogen (the zymogen of the protease plasmin), c) binding of LAP to cell surface mannose-6 (M6P) phosphate/IGF-II receptors, d) LTBP, and e) TGase, as antibodies and/or inhibitors of each of these reactants blocked latent TGF-beta activation. A number of other proteases, including MMP-2, MMP-9, plasmin, calpain, chymase, and elastase have subsequently been described as latent TGFβ activators (Koli, et al. (2001)).

A second mechanism for latent TGFβ activation involves the interaction of the matricellular protein thrombospondin (TSP-1) with latent TGFβ in a multi-molecular complex containing TSP-1 receptors as well as CD36, and, in some cases, plasmin. Latent TGFβ activation involves a direct interaction between TSP-1 and LAP and includes the tripeptide sequence RFK found in the TSP-1 type 1 repeats. This peptide is believed to interact with the conserved tetra peptide LSKL in the LAP amino terminus disrupting the non-covalent association between LAP and TGF-β. A tetra peptide KRFK will activate latent TGF-β in vitro and in vivo, whereas addition of the LAP peptide (LSKL) in excess blocks latent TGF-β activation. TSP-1 −/− mice show a partial, overlapping phenotype with TGF-β1 −/− mice with respect to enhanced inflammation. The administration of the LSKL blocking peptide to wild type mice induces pancreas and lung pathologies similar to those observed in TGF-β −/− animals, whereas the addition of the KRFK activating peptide to TSP-1 −/− mice reverts the phenotype towards normal. However, the phenotype of the TSP-1 −/− mouse does not replicate the full phenotype of the TGF-β1 −/− mouse nor does the TSP-1 −/− phenotype resemble any of the phenotypes of the TGF-β2 −/− or TGF-β3 −/− mice. These discrepancies again suggest that there may be multiple and isoform specific mechanisms for activation of latent TGF-3.

Latent TGF-β can be activated by mild acid (pH 4.5), which probably destabilizes the interaction between LAP and TGF-β. However, except for specialized situations, such as the extracellular compartment formed by osteoclasts during bone resorption, this pH is probably rarely achieved in the extracellular environment in vivo. Therefore, pH is unlikely to be a common mechanism for TGF-β activation.

The TGF-β1 and β3 propeptides, but not the TGF-β2 propeptide, contain the integrin recognition sequence RGD. TGF-β1 and TGF-β3 LAPs interact with cells expressing the integrins αvβ1 and αvβ5. Although the binding of latent TGF-β with these integrins does not result in activation, binding of latent TGF-β with αvβ6 results in activation (Munger et al. (1999) *Cell* 96:319). Activation of latent TGF-β1 or β by αvβ6 requires the RGD sequence as mutant forms of TGF-β1 or β3 containing RGE fail to be activated.

Integrin αvβ8, in combination with MT1-MMP, activates latent TGFβ (Mu et al. (2002) *J. Cell Biol.* 159:493). Integrin αvβ8 is expressed primarily in normal epithelia (e.g., airway epithelia), mesenchymal cells, and neuronal tissues. In what is considered a unique mechanism, αvβ8, expressed on the cell surface, interacts with latent TGFβ in the cell matrix, and recruits MT1-MMP to the complex, where the protease cleaves the latent TGFβ and releases the active, mature TGFβ peptide.

TGFβ Bioassay

To determine TGFβ activation in a coculture assay, test cells expressing αvβ8 are co-cultured with TMLC cells, which are mink lung epithelial cells stably transfected with a TGF-β responsive fragment of the plasminogen activator inhibitor-1 promoter driving the luciferase gene (Abe et al. (1994) *Annal Biochem* 216:276). TMLC cells are highly responsive to TGFβ and produce a very low background of TGFβ activation. TMLC cells can thus be used in coculture with other cell lines or cell-free fractions to test for the presence of active TGFβ using luminescence as a readout. Assays are performed in the presence or absence of anti-TGFβ-blocking antibody (10 μg/ml, 1D11; R&D Systems), anti-β8 (20 μg/ml, 37E1B5) or anti-β6 (150 μg/ml, 10D5) as described (Abe (1994); Munger (1999).

To measure active TGFβ in tumor tissue, equal weights of tumor tissue is minced and incubated in sterile DME for 30 min at 4° C. The supernatants containing active TGFβ are harvested after centrifugation (20 g) at 4° C. The pellets are then incubated in serum-free DME for 20 min at 80° C. to activate SLC after which the supernatants were harvested. The supernatants containing active or heat-activated (latent) TGFβ are then added to preplated TMLC cells with or without 1D11. For protease inhibitor assays, inhibitors are added at the initiation of the coculture. The maximal dose of each inhibitor are defined as the highest concentration that do not inhibit the ability of the TMLC cells to respond to recombinant active TGFβ. To measure soluble TGFβ activity from cultured cells, cells are incubated in 100 μl of complete medium with or without 37E1 or 10D5 for 1 h at 37° C. with gentle rotation. Cell-free supernatants are harvested by centrifugation (20 g) for 5 min at 4° C. and then added to preplated TMLC cells in the presence or absence of 1D11. For soluble receptor assays, conditioned medium obtained from overnight cultures of cells are used. Relative luciferase units are defined as activity minus the background activity of the TMLC reporter cells.

Antibodies of the Invention

The present invention provides antibodies that specifically bind to integrin αvβ8, but do not significantly bind to other integrins (e.g., αvβ6, αvβ3, etc.). Antibodies of the invention can bind to a specific epitope or epitope region within αvβ8. The epitope can be a conformational (non-linear) or nonconformational epitope. Such an antibody can bind to β8 alone, i.e., the epitope is located within β8. The binding of the antibody of the invention may require an epitope region outside β8, e.g., a conformational epitope, or one that is dependent upon elements from both within αv and within β8.

In some embodiments, the antibody binds to β8 and inhibits TGFβ activation, e.g., compared to TGFβ activation in the absence of the antibody. In some embodiments, the antibody does not reduce adhesion of cells expressing αvβ8 to TGFβ, that is, the antibody does not reduce αvβ8-mediated cell adhesion to TGFβ. In some embodiments, the antibody can reduce binding of soluble αvβ8 to TGFβ, compared to αvβ8 binding in the absence of the antibody. In some embodiments, the antibody can bind to an epitope on β8 that is within SEQ ID NO: 11. In some embodiments, the epitope includes at least one amino acid selected from amino acids R79, I85, S95, P100, I108, P109, R128, H140, and F179 of human β8. In some embodiments, the epitope includes at least one amino acid selected from amino acids 174, N88, I107, T110, I125, R175, and F180 of human β8. In some embodiments, the epitope includes at least one amino acid selected from amino acids I125, R128, R175, F179, and F180 of human β8. In some embodiments, the antibody binds human, but not mouse β8.

The binding site, i.e., epitope, of an antibody raised against a given antigen can be determined using methods known in the art. For example, a competition assay (e.g., a competitive ELISA) can be carried out using an antibody with a known epitope. If the test antibody competes for antigen binding, then it likely shares at least part of the same epitope. The epitope can also be localized using domain swapping or selective mutagenesis of the antigen. That is, each region, or each amino acid, of the antigen can be "swapped" out, or substituted with amino acids or components that are known to not interact with the test antibody. If substitution of a given region or amino acid reduces binding of the test antibody to the substituted antigen compared to the non-substituted antigen, then that region or amino acid is likely involved in the epitope.

The invention provides antibodies that selectively perturb the αvβ8-mediated activation of TGF-β (e.g., release of mature, active TGFβ from latent TGFβ at the cell surface) but, in some embodiments, the antibody does not interfere significantly with adhesion of αvβ8 (e.g., on an αvβ8-expressing cell) to latent TGFβ. Some antibodies are characterized by a high degree of selectivity in perturbing only integrin αvβ8-mediated activation of TGF-β and not the cell adhesion properties, which may be undesirable to inhibit. Some antibodies block TGFβ activation locally where integrin αvβ8 is expressed.

An exemplary antibody of the invention has a light chain variable region comprising three light chain CDRs of SEQ ID NO: 5, SEQ ID NO: 6, and SEQ ID NO: 7, and a heavy chain variable region comprising three heavy chain CDRs of SEQ ID NO: 8, SEQ ID NO: 9, SEQ ID NO: 10. Antibodies of the present invention also include an antibody competes for binding to αvβ8 with an antibody having a light chain variable region comprising three light chain CDRs of SEQ ID NO: 5, SEQ ID NO: 6, and SEQ ID NO: 7, and a heavy chain variable region comprising three heavy chain CDRs of SEQ ID NO: 8, SEQ ID NO: 9, SEQ ID NO: 10. The first residue for SEQ ID NO: 9 can be either R or Y. It is contemplated that other conservative substitutions of R or Y would also work. The isotype of the antibody can be IgG1, IgG2, IgG2a, IgG3 or IgG4.

Accordingly, antibodies of the present invention can be an antibody having a light chain variable region of either SEQ ID NO: 3 or SEQ ID NO: 4 and a heavy chain variable region of either SEQ ID NO:1 or SEQ ID NO: 2. In some embodiments, antibodies of the present invention has a light chain variable region of SEQ ID NO:3 and a heavy chain variable region of SEQ ID NO: 1. In some embodiments, antibodies of the present invention has a light chain variable region of SEQ ID NO:4 and a heavy chain variable region of SEQ ID NO:2. Two exemplary antibodies are 37E1 and 37E1B5.

Antibodies of the present invention can be polyclonal or monoclonal. Polyclonal sera typically contain mixed populations of antibodies specifically binding to several epitopes along the length of αvβ8. However, polyclonal sera can be specific to a particular segment of αvβ8. Exemplary antibodies are chimeric, humanized (see Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539), or human (Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991)) EP1481008, Bleck, Bioprocessing Journal 1 (September/October 2005), US2004132066, US2005008625, WO2004072266, WO2005065348, WO2005069970, and WO2006055778. In some embodiments, the antibodies are humanized or chimeric forms of 37E1, or 37E1B5. Human isotype IgG1, IgG2, IgG3 or IgG4 can be used for humanized or chimeric antibodies. Some antibodies specifically bind to αvβ8 with a binding affinity greater than or equal to about $10^7$, $10^8$, $10^9$, $10^{10}$, $10^{11}$, or $10^{12}$ M$^{-1}$.

Antagonists of Integrin αvβ8

It is further contemplated that various antagonists of integrin αvβ8, naturally occurring or synthetic, can be used. Such antagonists include, e.g., peptides or small molecules. Antagonists can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules. In some embodiments, the antagonist of integrin αvβ8 is a TGFβ-specific peptide, e.g., a TGFβ1-specific peptide or a TGFβ3-specific peptide. Examples of TGFβ-specific peptides include, but are not limited to, a peptide comprising GRRGDLATIH (Mu et al. (2002) *Journal of Cell Biology* 157:493-507), and a peptide comprising HGRGDLGRLK. In some embodiments, the antagonist reduces TGFβ activation but does not significantly inhibit αvβ8-mediated cell adhesion to TGFβ.

Indications

It is contemplated that the anti-αvβ8 antagonists, anti-αvβ8 antibodies or immunoconjugates, compositions, and methods of the present invention may be used to detect, treat, or prevent chronic obstructive pulmonary disease (COPD) and asthma.

It is further contemplated that the anti-αvβ8 antagonists, anti-αvβ8 antibodies or immunoconjugates, compositions, and methods of the present invention may be used to detect, treat, or prevent an inflammatory brain autoimmune disease, multiple sclerosis, a demylinating disease (e.g., transverse myelitis, Devic's disease, Guillain-Barré syndrome), neuroinflammation, kidney disease, or glioma.

It is further contemplated that the anti-αvβ8 antagonists, anti-αvβ8 antibodies or immunoconjugates, compositions, and methods of the present invention may be used to detect, treat, or prevent arthritis.

It is further contemplated that the anti-αvβ8 antagonists, anti-αvβ8 antibodies or immunoconjugates, compositions, and methods of the present invention may be used to detect, treat, or prevent various fibrotic disorders, such as airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, cryptogenic organizing pneumonia, chronic hypersensitivity pneumonia, drug-related lung fibrosis, renal fibrosis, liver fibrosis.

It is further contemplated that the anti-αvβ8 antagonists, anti-αvβ8 antibodies or immunoconjugates, compositions, and methods of the present invention may be used to detect, treat, or prevent adenocarcinoma, squamous carcinoma, breast carcinoma, and cancer growth and metastasis.

Diagnostic Compositions

The detectable moiety can be associated with an antibody of the invention, either directly, or indirectly, e.g., via a chelator or linker. A labeled antibody can then be provided to an individual to determine the applicability of an intended therapy. For example, a labeled antibody may be used to detect the integrin β8 density within the diseased area, where the density is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.).

A diagnostic agent comprising an antibody of the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include 11In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{53}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl]benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclotetradecane-1,4,8,11-tetraacetic acid (TETA), 1,4,7,10-tetraazacyclododecane-1,4,7,10-tetraacetic acid (DOTA), N$^1$,N$^1$-bis(pyridin-2-ylmethyl)ethane-1,2-diamine (ENPy2) and derivatives thereof.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

Methods of Administration and Formulation

The anti-αvβ8 antagonists, anti-αvβ8 antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical (e.g., transdermal), or inhalation routes. Intravenous or subcutaneous administration of the antibody is preferred. The administration may be local or systemic.

The compositions for administration will commonly comprise an agent as described herein (e.g., anti-$\alpha v \beta 8$ antagonists, anti-$\alpha v \beta 8$ antibodies and immunoconjugates) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly(2-hydroxyethyl-methacrylate), or poly(vinylalcohol)), polylactides. The antibodies and immunoconjugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer, fibrosis, COPD, arthritis, etc.) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of an $\alpha v \beta 8$ can be useful in reducing TGF$\beta$ activation in an individual. Anti-$\alpha v \beta 8$ antagonists, anti-$\alpha v \beta 8$ antibodies or immunoconjugates can be administered alone or co-administered in combination with conventional chemotherapy, radiotherapy or immunotherapy as well as currently developed therapeutics.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more anti-αvβ8 antagonists, anti-αvβ8 antibodies or immunoconjugates, optionally in combination with one or more chemotherapeutic agents or immunotherapeutic agents, in a sustained release formulation.

In therapeutic use for the treatment of cancer, anti-αvβ8 antagonists, anti-αvβ8 antibodies or immunoconjugates utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations (e.g., anti-αvβ8 antagonists, anti-αvβ8 antibodies or immunoconjugates) for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

EXAMPLES

The following examples are offered to illustrate, but not limit the claimed invention.

Example 1. Investigating the Role of Integrin αvβ8 in Airway Remodeling

Transforming growth factor-beta, (TGF-β), is a cytokine involved in the inflammatory and fibrotic response. We have previously shown that IL-1β upregulates expression of β8, and that β8 expression is increased in the airways of COPD patients. However, the interactions of β8, TGF-β, and IL-1β are poorly understood in vivo, leading us to develop a mouse model of β8-mediated airway remodeling. Here we show that the IL-1-β induced, β8-mediated activation of TGF-β plays a critical role in airway remodeling.

The role of β8 in mediating airway remodeling was addressed by deletion of β8 by using a Cre/LoxP system, using intratracheal adenoviral IL-1β as a model for inflammation. Six- to 9-week old mice with one floxed integrin β8 allele and one knockout allele (Floxed/−) in a C57Bl/6 background were used. Either adenoviral human IL-1β (Ad-hIL-1β) or control adenovirus was instilled intratracheally with or without Ad-Cre. In addition, mice expressing the Cre-ER(T) fusion recombinase under control of the Collagen Iα2 promoter were used to show that fibroblasts play a major role in αvβ8-mediated activation of TGF-β in bleomycin induced lung fibrosis, ovalalbumin induced airway remodeling, and Ad-IL1β-induced airway remodeling. Airway morphometry changes were evaluated using histology, and analysis of gene expression of several inflammatory cytokines at multiple time points after Ad-hIL-1β administration revealed sequential induction of genes that characterize an inflammatory response.

In the β8 conditional knock out model, β8 is required for human IL-1β induced transient airway inflammation and fibrosis. Addition of human IL-1β leads to β8-mediated activation of TGF-β, induction of the mouse ccl2 and ccl20 genes, recruitment of dendritic cells and initiation and perpetuation of the adaptive immune response.

These data show that the conditional deletion of integrin β8 resulted in decreased inflammation and fibrotic response to both Ad-hIL-1β and ovalbumin, which resulted in protection from airway remodeling. We identify a pivotal role for IL-1β induced or ovalbumin-induced, β8-mediated TGF-β activation in airway remodeling, and for bleomycin-induced acute lung injury.

Example 2. Antibody 37E1

We have created a mouse monoclonal antibody (named clone 37E1, isotype IgG2a) that selectively blocks the interaction of the human integrin αvβ8 with its ligand, transforming growth factor-β (TGF-β). TGF-β is ubiquitously expressed in three isoforms in mammals (TGF-β 1-3), but is maintained in an inactive form by its non-covalent interaction with its propeptide, the latency associated domain of TGF-β (LAP). The integrin αvβ8 binds to the LAP of TGF-β and mediates the activation of TGF-β1 and 3. Germline or conditional genetic deletion studies have revealed that integrin αvβ8-mediated activation of TGF-β is essential for the in vivo activation of TGF-β and thus αvβ8 is a "gatekeeper" of TGF-β function. In particular, integrin αvβ8-mediated activation of TGF-β is likely involved in the pathogenesis of COPD, pulmonary fibrosis, renal fibrosis, inflammatory brain autoimmune diseases (multiple sclerosis and demylinating diseases), neuroinflammation, kidney disease, and cancer growth and metastasis. In general, integrins are adhesion molecules and mediate the attachment of cells to extracellular matrix proteins. Clone 37E1 is distinct in that it selectively perturbs the αvβ8-mediated activation of TGF-β and not the binding of αvβ8 to immobilized or secreted TGF-β. This affords a high degree of selectivity in perturbing only integrin αvβ8-mediated activation of TGF-β activation and not the cell adhesion properties, which may be undesirable to inhibit. In addition, global inactivation of TGF-β is likely to have undesirable side effects since TGF-β is an essential homeostatic epithelial, and immune effector.

Example 3. Antibody 37E1B5

We have engineered the variable regions of the heavy and light chains of clone 37E1, and used random mutagenesis and chain shuffling in the yeast display system to make higher affinity antibodies. We have identified specific amino acid substitutions that confer higher affinity for the same antigen, and we have broadly classified these mutations according to function. One of those mutants was named 37E1B5. It shows increased affinity in vitro and stronger efficacy in inhibiting integrin αvβ8-mediated activation of TGF-β in cultured cells. The effective therapeutic dose of the 37E1B5 antibody in vitro is in the picomolar range. For better diagnostic and therapeutic application, we created three versions of 37E1B5: mouse IgG1, mouse IgG2a, and partially humanized IgG1. All were produced in transformed CHO cells.

Example 4. Generation of ITGB8 BAC Transgenic Mice

We have created a humanized BAC transgenic mouse expressing human β8 and crossed it to β8 ko mice to rescue the lethal effects of murine integrin αvβ8 deletion. This humanized mouse will be used to test the toxicity and efficacy of high affinity clones in lung, brain, liver, and kidney disease models.

Clone RP11-431K20 which contains 72315 5' and 30,683 3' of the respective 5' and 3' flanking regions of the ITGB8 gene was obtained as a bacterial stab culture from (Children's Hospital Oakland Research Institute, Oakland, Calif.). Plates (LB with chloramphenicol, 12.5 μg/ml) were streaked and colonies selected using colony PCR employing primers designed to the 5' and 3' BAC ends. Sequence was confirmed in the 5' and 3' ends, the 5' UTR into the first intron, the $9^{th}$ exon into the $9^{th}$ intron and the 10th exon/intron region. An individual colony was grown up and BAC plasmid DNA isolated (Nucleobond). The plasmid was linearized with PI-Sce (NEB), purified over a NAPS column and subject to pulse field electrophoresis to confirm the concentration and integrity of the DNA. The DNA was injected into FVB/N embryos in the UCSF Cancer Center Transgenic Facility. From over two hundred injected embryos, 24 pups were obtained of which 4 were identified as founders by tail DNA PCR using 5' and 3' BAC end primers.

Three of these lines (B, C and D) provided germ line transmission. Lines B, C, and D have been crossed to itgb8 C57B/6 mice engineered to have one itgb8 allele knocked-out. The F2 generation has been crossed to obtain ITGB8 BAC tg mice on an itgb8 −/− background.

These mice (lines B, C, and D) display no gross phenotypic abnormalities at 3 or 6 months of age. These results demonstrate that all of the requisite regulatory elements are confined to the upstream and downstream elements contained in BAC RP11-431K20 to provide appropriate tissue expression to rescue the lethal phenotype of the itgb8 −/− mice. These mice also provide an experimental system to determine biomarkers, further investigate disease mechanisms in vivo, model human disease, and test the effects of therapeutics directed against αvβ8-mediated TGF-β activation.

Example 5. Neutralizing Anti-Integrin β8 Reduces ColI

Increased ECM production and increased fibroblast contractility are hallmarks of fibrotic responses seen in airway wall thickening, and increased type I collagen (Col I) and increased SMA (aSMA) are key biochemical markers of that response. To assess the contribution of autocrine αvβ8-mediated TGF-β activation to the profibrotic fibroblast phenotype, we used neutralizing anti-β8. Autocrine αvβ8-mediated activation of TGF-β influenced the myofibroblast phenotype, since treatment of airway fibroblasts with β8 blocking antibodies inhibited aSMA expression and Col I secretion. Coculture of airway fibroblasts with squamous metaplastic human bronchial epithelial cells led to an increase in Col I transcription and protein production by airway fibroblasts. The increased production of collagen was IL-1β- and fibroblast β8-dependent. The increase in Col I expression induced by coculture with squamous metaplastic human bronchial epithelial cells could be almost completely inhibited by treatment of cocultures with IL-1RA, or by transfection of airway fibroblasts with β8 siRNA.

Example 6. Characterization of 37E1B5 Epitope

Chimeric integrin β8 constructs, which swapped mouse sequences into human ITGB8 were used to localize the 37E1B5 binding epitope. The epitope was localized by antibody binding, cell surface staining, and detection by flow cytometry. The 37E1B5 epitope is encompassed within amino acids 74-180 of human integrin β8. 37E1B5 binds to human, but not to mouse β8. Therefore, at least one of the 9 non-conservative amino acid differences or 7 minor amino acid differences (indicated by + in the middle line of the sequence) are included in the binding epitope. These domains reflect portions of what are known in the field as the Psi, hybrid and the alpha1 helix of the Beta-I domain of the integrin β8 subunit, and are found on the surface of the molecule.

robust airway remodeling with an immunological profile similar to human chronic obstructive lung disease is reproducibly induced.

We found that the 37E1B5 antibody, at a dose of 7 mg/kg, significantly blocked airway inflammation, with a significant reduction in neutrophils in the bronchioalveolar lavage. Histologically, airway wall inflammation and fibrosis was significantly decreased by 37E1B5. These data complement

```
M itgb8 74    VSGGSGSERCDTVSSLISKGCPVDSIEYLSVHVVTSSENEINTQVTP            120

+SGGS SERCD VS+LISKGC VDSIEY SVHV+  +ENEINTQVTP

H ITGB8 74    ISGGSRSERCDIVSNLISKGCSVDSIEYPSVHVIIPTENEINTQVTP            120

M itgb8       GEVSVQLHPGAEANFMLKVRPLKKYPVDLYYLVDVSASMHNNIEKLNSVGNDLSKKMALY 180

GEVS+QL PGAEANFMLKV PLKKYPVDLYYLVDVSASMHNNIEKLNSVGNDLS+KMA +

H ITGB8       GEVSIQLRPGAEANFMLKVHPLKKYPVDLYYLVDVSASMHNNIEKLNSVGNDLSRKMAFF 180
```

SEQ ID NO:11 represents the region of human integrin β8 that includes the 37E1B5 epitope (amino acids 74-180). SEQ ID NO:12 represents the homologous murine sequence, which is not bound by the 37E1B5 antibody. The R at position 140 of the murine sequence is polymorphic, and can also be an H.

We performed further domain swapping studies within this region, substituting murine sequence for human, to determine which amino acid(s) are included in the 37E1B5 epitope. We found that substituting murine amino acids 125-180 of Integrin β8 significantly reduced 37E1B5 binding. Thus, the epitope on human Integrin β8 includes at least one amino acid selected from I125, R128, R175, F179, and F180.

Example 7. Integrin 38 Expression in COPD Fibroblasts

We found that Integrin β8 expression is increased in fibroblasts from the lungs of human COPD patients, as demonstrated by tissue staining and primary culture. In addition, Integrin β8 expression is significantly increased in fibroblasts isolated from patients with idiopathic pulmonary fibrosis compared to fibroblasts from normal patients. We have also found that COPD fibroblasts have increased IL-1β-dependent integrin αvβ8 protein expression compared to normal lung fibroblasts. These data demonstrate that αvβ8 is both a downstream target and pathologic mediator of IL-1β effects.

The 37E1B5 antibody can be used therapeutically and diagnostically in diseases where Integrin β8 is expressed, and IL-1β and/or TGF-β play a pathologic role.

Example 8. Integrin 38 Neutralizing Antibody Reduces Induced Airway Inflammation We generated three lines of BAC transgenic mice using the human BAC clone RP11-431K20. These mice were bred to mice with one functional allele of mouse itgb8 to generate an F1 generation of mice with human ITGB8 and one functional copy of mouse itgb8. These mice were cross bred to generate an F2 generation that resulted in viable BAC ITGB8, that is, itgb8 −/− mice with a human copy of the gene, demonstrating rescue of itgb8 −/− lethality.

These mice were used to induce airway remodeling using an intratracheal adenoviral-IL-1β delivery model. In this adenoviral-IL-1β-induced airway wall inflammation model, other data showing that fibroblast-specific deletion of itgb8 can significantly inhibit adenoviral-IL-1β-induced airway remodeling.

We also found that allergic airway remodeling (ovalbumin-induced airway inflammation, fibrosis and mucous metaplasia), is greatly diminished in mice with fibroblast-specific deletion of itgb8. The allergic model is also dependent on both IL-1β and TGF-3. These data imply a general role for itgb8 in amplification of both pathologic innate and adaptive immune responses where IL-1β and TGF-β play a role. IL-1β causes an increase in integrin β8 in multiple cell-types, including fibroblasts from the airway and lung, and astrocytes. This IL-1β induced integrin β8 expression is observed in both mice and humans.

Example 9. Human Articular Chondrocytes Express Integrin αvβ8

Adult articular cartilage was harvested from the joint space of knee from a patient undergoing elective repair of a knee for chronic osteoarthritis. Primary chondrocytes were grown to 70% confluence and the integrin receptor expression determined by cell staining and flow cytometry. The antibodies used were anti-β8 (37E1B5), and anti-β6 (E7P6). Robust staining was detected with 37E1B5 and no staining was seen with E7P6. Primary chondrocytes were co-cultured with TMLC TGF-β reporter cells (Annes et al. (2004) *J. Cell Biol.* 165:723) in a TGF-β bioassay in the presence or absence of anti-β8 (37E1B5) or neutralizing anti-β6. Anti-β8 produced a robust blockade of TGF-β activation while anti-β6 produced no such effect.

The results indicate not only that αvβ8 is expressed in chondrocytes, but that the expression results in TGFβ activation. Thus, inhibition of αvβ8 can be used to treat cartilage disorders related to activated TGFβ, such as arthritis and synovial fibrosis (see, e.g., Bakker et al. (2001) *Osteoarthritis and Cartilage* 9:128).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing TGFβ activation in an individual, the method comprising administering an antibody that specifically binds αvβ8, wherein the antibody comprises a heavy chain variable region that comprises a CDR1 sequence of SEQ ID NO: 5, a CDR2 sequence of SEQ ID NO: 6, and a CDR3 sequence of SEQ ID NO: 7, and a light chain variable region that comprises a CDR1 sequence of SEQ ID NO: 8, a CDR2 sequence of SEQ ID NO: 9, wherein Xaa in SEQ ID NO:9 is tyrosine, and a CDR3 sequence of SEQ ID NO: 10, thereby reducing TGFβ activation in the individual.

2. The method of claim 1, wherein the antibody has a heavy chain variable region of SEQ ID NO: 2 and a light chain variable region of SEQ ID NO: 4.

3. The method of claim 1, wherein the isotype of the antibody is IgG1, IgG2, IgG3 or IgG4.

4. The method of claim 1, wherein the antibody is a monoclonal antibody.

5. The method of claim 1, wherein the antibody is a human antibody.

6. The method of claim 1, wherein the individual is a human.

7. The method of claim 1, wherein the individual has at least one condition selected from the group consisting of chronic obstructive pulmonary disease (COPD), asthma, arthritis, and a pulmonary fibrotic disorder.

8. The method of claim 1, wherein the antibody has a kappa light chain variable region and a gamma heavy chain variable region.

9. The method of claim 1, wherein the antibody has a lambda light chain variable region and a gamma heavy chain variable region.

10. The method of claim 1, wherein the antibody is a humanized antibody.

11. The method of claim 1, wherein the antibody is a chimeric antibody.

* * * * *

UNITED STATES PATENT AND TRADEMARK OFFICE
CERTIFICATE OF CORRECTION

PATENT NO. : 9,845,357 B2
APPLICATION NO. : 15/003642
DATED : December 19, 2017
INVENTOR(S) : Stephen Nishimura et al.

It is certified that error appears in the above-identified patent and that said Letters Patent is hereby corrected as shown below:

Column 1 Lines 21-24 should read:
This invention was made with Government support under Grant No. HL063993 and NS044155 awarded by the National Institutes of Health. The Government has certain rights in this invention.

Signed and Sealed this
Twentieth Day of March, 2018

Andrei Iancu
*Director of the United States Patent and Trademark Office*